US00PP18408P2

(12) United States Plant Patent
Yokoi

(10) Patent No.: US PP18,408 P2
(45) Date of Patent: Jan. 8, 2008

(54) ***HYPERICUM* PLANT NAMED 'STARDUST'**

(50) Latin Name: *Hypericum patulum*
Varietal Denomination: Stardust

(75) Inventor: Masato Yokoi, Kawaguchi (JP)

(73) Assignee: Its Aul Plants, LLC, Atlanta, GA (US)

( * ) Notice: Subject to any disclaimer, the term of this patent is extended or adjusted under 35 U.S.C. 154(b) by 3 days.

(21) Appl. No.: 11/516,868

(22) Filed: Sep. 7, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Hypericum patulum,* 'Stardust', characterized by its unique foliage coloration with new foliage emerging creamy white tinged with pink, changing to creamy white foliage heavily mottled with dark green, and turning dark green as the leaf matures. The vigorous growth habit and pendant stems of 'Stardust' make it suitable for both containers and use as a landscape plant.

2 Drawing Sheets

Botanical classification: *Hypericum patulum.*
Variety denomination: 'Stardust'.

BACKGROUND OF THE INVENTION

The present invention relates to a new and distinct cultivar of *Hypericum patulum,* and will be referred to hereafter by its cultivar name, 'Stardust'. 'Stardust' is an evergreen shrub grown for use as a landscape plant and container plantings.

The new cultivar of *Hypericum* was discovered as a naturally occurring branch mutation of an unnamed plant of *Hypericum patulum* by the inventor in summer of 1990 in Angyo, Japan. 'Stardust' was selected as unique primarily for its unique foliage coloration and plant habit.

Asexual reproduction of the new cultivar was first accomplished by terminal stem cuttings at Hyogo, Japan in June of 2002. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot for three years in Atlanta, Ga. These attributes in combination distinguish 'Stardust' as a unique cultivar of *Hypericum.*

1. 'Stardust' has unique foliage coloration with new foliage emerging creamy white tinged with pink, maturing foliage turning creamy white with heavy mottling of dark green, and turning to solid green when the foliage is mature.
2. The new growth of 'Stardust' emerges with creamy white stems tinged with pink. The newly formed stems of the parent plant are light green.
3. 'Stardust' exhibits a more procumbent plant habit in comparison to its parent.
4. 'Stardust' exhibits a vigorous growth habit.

'Stardust' is unique and unlike any other cultivars of *Hypericum.* The parent plant, *Hypericum patulum,* has solid green foliage and a more upright growth habit. The only variety of *Hypericum patulum* with uniquely colored foliage known to the inventor, *Hypericum patulum* 'Variegatum' (not patented), has green leaves with a thin white margin. *Hypericum* 'Tricolor' (not patented), a hybrid *Hypericum,* has variegated foliage with pink and white margins rather than the changing foliage color of 'Stardust'.

BRIEF DESCRIPTION OF THE DRAWING

The accompanying colored photographs were taken in July and illustrate the overall appearance and distinct characteristics of the new *Hypericum* as grown in Atlanta, Ga.

The photograph in FIG. 1 illustrates the plant habit and foliage coloration as grown in a two-gallon container for two years under greenhouse conditions.

Figure 1:
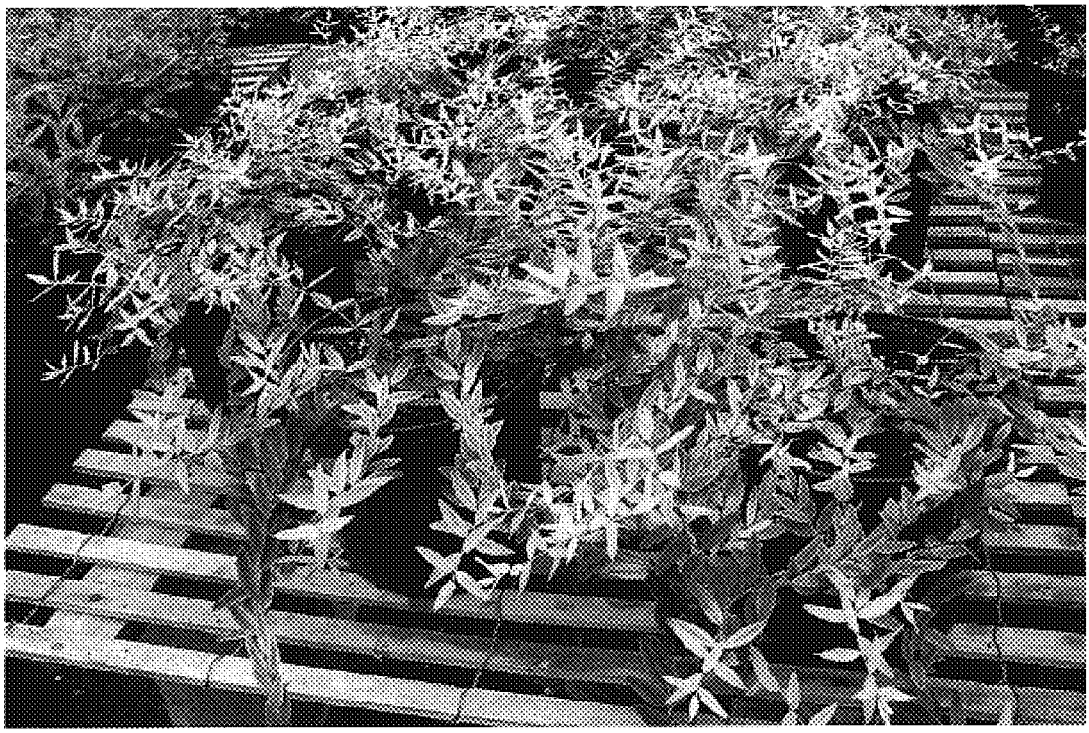
Figure 2:
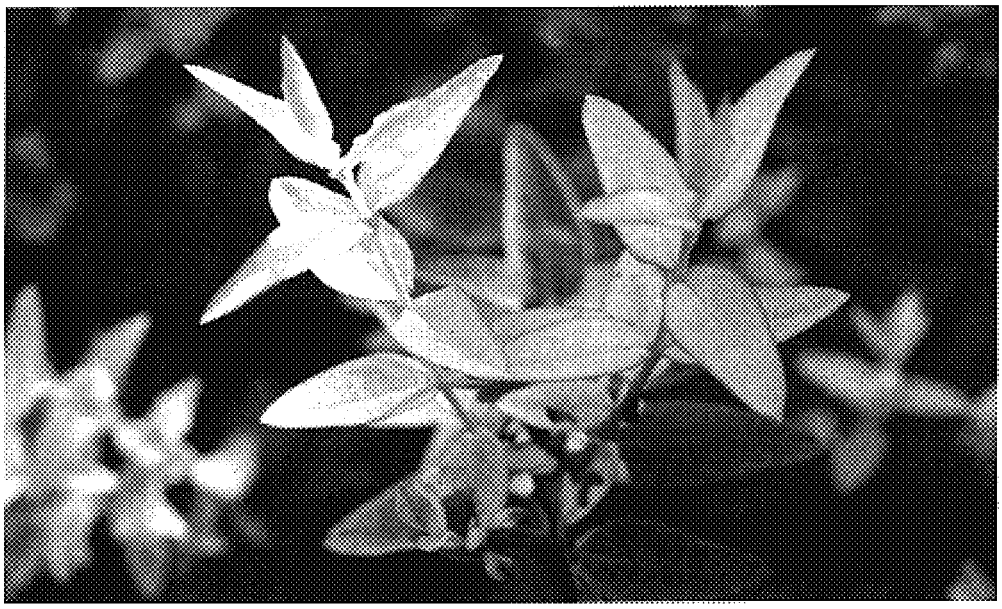
Figure 3:
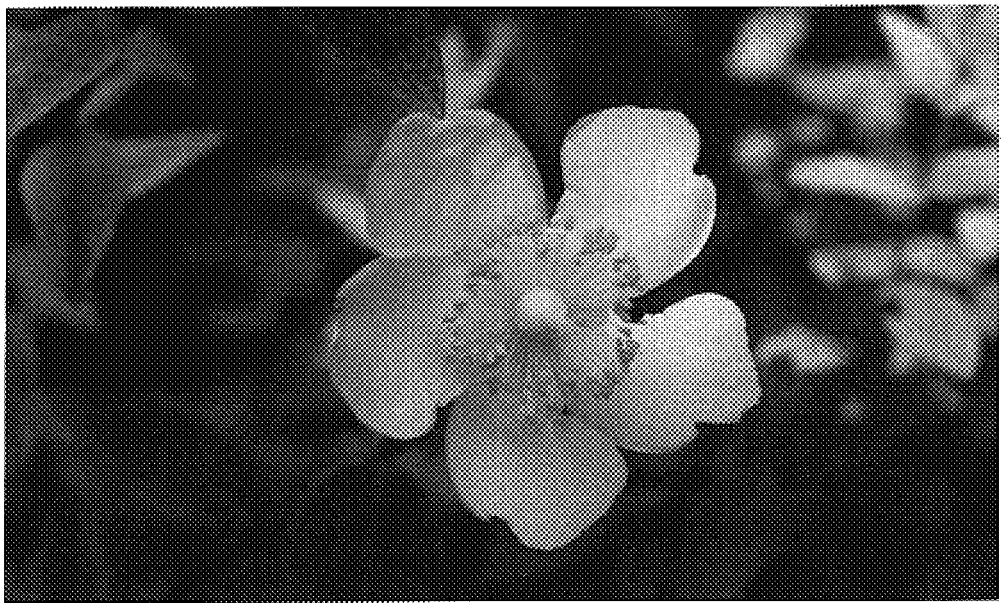

The photographs in FIG. 2 and FIG. 3 were taken of a plant grown outdoors for three years in a trial garden.

The photograph in FIG. 2 illustrates the habit and coloration of newly formed stems and foliage and the photograph in FIG. 3 is a close-up view of a typical flower.

The colors in the photographs are as close as possible with the digital photography techniques available, the color values cited in the detailed botanical description accurately describe the colors of the new *Hypericum.*

DETAILED BOTANICAL DESCRIPTION

The following is a detailed description of the new cultivar as grown outdoors in partial shade in a trial garden in Atlanta, Ga. for three years. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Stardust' is a cultivar of *Hypericum patulum.*

*Parentage.*—Naturally occurring branch mutation of an unnamed plant of *Hypericum patulum.*

*Blooming period.*—Blooms for approximately 4 weeks, typically from mid June to mid July.

*Plant habit.*—Initially upright with branches becoming pendant, semi-evergreen in Atlanta, Ga.

*Height and spread.*—Reaches about 1.2 m (4 ft) in height and about 1.5 m in width (5 ft.).

*Cold hardiness.*—U.S.D.A. Zones 6 to 9.

*Diseases and pests.*—No susceptibility or resistance to diseases or pests known to affect *Hypericum* has been observed for 'Stardust'.

*Root description.*—Fibrous, freely branched.

Growth and propagation:

*Propagation.*—Terminal, softwood stem cuttings.

*Root initiation.*—Roots develop in 3 weeks in summer under greenhouse conditions under intermittent mist without supplemental lighting.

*Time required for root development.*—6 weeks to develop a 72-cell plug from a rooted cutting.

*Growth rate.*—Vigorous.

Stem description:

*Shape.*—Round.

*Stem color.*—New growth emerges 165C with new side shoots 158C blushed with 62C, maturing branches become 165A as they become woody.

*Stem size.*—Main stems; up to about 2.5 cm in diameter, lateral branches; up to about 50 cm in length and 4 mm in width.

*Stem surface.*—Glabrous.

*Internode length.*—Average of 1 cm.

*Branching.*—Freely branched with lateral branches cascading with an open habit.

Foliage description:

*Leaf shape.*—Ovate-oblong.

*Leaf division.*—Simple.

*Leaf base.*—Cuneate.

*Leaf apex.*—Acute.

*Leaf fragrance.*—None.

*Leaf venation.*—Pinnate, not prominent or conspicuous, same as leaf color.

*Leaf margins.*—Entire.

*Leaf arrangement.*—Opposite, aspect is horizontal.

*Leaf attachment.*—Sessile.

*Leaf substance.*—Thick on mature leaves.

*Leaf surface.*—Glabrous, slightly pubescent on lower surface.

*Leaf size.*—Up to about 4.5 cm in length, up to about 1.8 cm in width.

*Leaf color.*—Newly expanded leaves (upper surface and lower surface); emerges 158C becoming 158C blushed with 62C, maturing leaves; upper surface 144D heavily overlaid with mottling of 137A to 137D, lower surface 158A heavily mottled with 191A to 191C, mature leaves; upper surface 137A (slightly darker), lower surface 191A overlaid with 191B.

Inflorescence description:

*Inflorescence type.*—Cyme of approximately 3 to 5 cup-shaped flowers or solitary flowers from terminal and upper nodes.

*Flower buds.*—Conical in shape with acute apex, up to 1.5 cm in length and 1 cm in width prior to opening, calyx portion is wrapped around petals and 145C in color, petal portion emerges N144B in color and changes to 9A prior to opening.

*Flower fragrance.*—None detected.

*Flower quantity.*—About 10 to 12 per branch.

*Flower type.*—Complete, cup-shaped.

*Flower aspect.*—Outward facing.

*Flower size.*—Average of 6 cm in diameter and 1.5 cm in depth.

*Petals.*—5, subcircular in shape with 2 irregularly placed indentations, un-fused but overlapping at base, curved inward, upper surface is glabrous and lower surface is shiny, entire margin, rounded base, rounded to retuse apex, about 2.5 cm in length and 2 cm in width, color is 9A (opening and mature, lower and upper surface).

*Calyx.*—Flat in shape, sepals free but overlapping at base, about 2 cm in diameter and 2 mm in depth.

*Sepals.*—5, broadly elliptic (almost round) in shape, 145C in color, glabrous surface, about 7 mm in length and 7 mm in width, entire margin, round apex and base.

*Peduncles.*—About 2.5 cm in length, 1.5 mm in width, 145C in color, glabrous surface.

*Pedicels.*—About 2 cm in length, 1.5 mm in width, 145C in color, glabrous surface.

Reproductive organs:

*Gynoecium.*—Compound pistil about 1 cm in length and 6 mm in width, styles 5 are 2C in color and about 8 mm in length and 1 mm in length, stigmas 5, 2A in color with branches about 3 mm in length and 0.7 mm in width, ovary is superior and 155B in color.

*Androcoecium.*—Numerous stamens (about 200), spreading to form a ring at base of ovary extending about 2.5 cm in diameter, filaments are 9A in color, about 9 mm in length and 0.3 mm, anthers are 16A in color, basifixed, about 2 mm in length and 1 mm in width, pollen was not visible.

*Fruit and seed.*—Fruit set was not observed for the new *Hypericum.*

I claim:

1. A new and distinct cultivar of *Hypericum* plant named 'Stardust' as herein illustrated and described.

* * * * *